United States Patent
Chen et al.

(10) Patent No.: US 8,633,323 B2
(45) Date of Patent: Jan. 21, 2014

(54) PROCESS FOR PREPARING BIS(THIOHYDRAZIDE AMIDES)

(75) Inventors: Shoujun Chen, Bedford, MA (US); Jun Jiang, Norwood, MA (US); Lijun Sun, Harvard, MA (US); Keizo Koya, Chestnut Hill, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 499 days.

(21) Appl. No.: 12/934,903

(22) PCT Filed: Mar. 31, 2009

(86) PCT No.: PCT/US2009/001996
§ 371 (c)(1),
(2), (4) Date: Dec. 22, 2010

(87) PCT Pub. No.: WO2009/123704
PCT Pub. Date: Oct. 8, 2009

(65) Prior Publication Data
US 2011/0098476 A1   Apr. 28, 2011

Related U.S. Application Data

(60) Provisional application No. 61/072,466, filed on Mar. 31, 2008.

(51) Int. Cl.
*C07D 213/44* (2006.01)
*C07C 327/00* (2006.01)

(52) U.S. Cl.
USPC .......................................... 546/262; 564/74

(58) Field of Classification Search
USPC .......................................... 546/262; 564/74
See application file for complete search history.

(56) References Cited

U.S. PATENT DOCUMENTS

| | | | |
|---|---|---|---|
| 6,762,204 B2 | 7/2004 | Koya et al. |
| 6,800,660 B2 | 10/2004 | Koya et al. |
| 6,825,235 B2 | 11/2004 | Chen et al. |
| 6,924,312 B2 | 8/2005 | Koya et al. |
| 7,001,923 B2 | 2/2006 | Koya et al. |
| 7,037,940 B2 | 5/2006 | Koya et al. |
| 7,074,952 B2 | 7/2006 | Chen et al. |
| 7,345,094 B2 | 3/2008 | Koya et al. |
| 7,368,473 B2 | 5/2008 | Koya et al. |
| 7,385,084 B2 | 6/2008 | Koya et al. |
| 7,435,843 B2 | 10/2008 | Chen et al. |
| 7,579,503 B2 | 8/2009 | Koya et al. |
| 7,645,904 B2 | 1/2010 | Chen et al. |
| 7,652,168 B2 | 1/2010 | Chen et al. |
| 7,671,092 B2 | 3/2010 | Koya et al. |
| 7,678,832 B2 | 3/2010 | Lunsmann et al. |
| 7,709,683 B2 | 5/2010 | Chen et al. |
| 7,750,042 B2 | 7/2010 | Koya et al. |
| 7,763,658 B2 | 7/2010 | Koya et al. |
| 7,795,313 B2 | 9/2010 | Koya et al. |
| 2006/0142386 A1 | 6/2006 | Barsoum |
| 2006/0142393 A1 | 6/2006 | Sherman et al. |
| 2006/0167106 A1 | 7/2006 | Zhang et al. |
| 2007/0088057 A1 | 4/2007 | Lunsmann et al. |
| 2008/0118562 A1 | 5/2008 | Koya |
| 2008/0119440 A1 | 5/2008 | Koya |
| 2008/0176828 A1 | 7/2008 | Williams et al. |
| 2008/0226588 A1 | 9/2008 | McLeod |
| 2009/0023736 A1 | 1/2009 | Koya et al. |
| 2009/0042991 A1 | 2/2009 | Barsoum et al. |
| 2009/0093538 A1 | 4/2009 | Bertin et al. |
| 2009/0137682 A1 | 5/2009 | Dahl |
| 2010/0068174 A1 | 3/2010 | Jacobson |
| 2010/0081635 A1 | 4/2010 | Chen et al. |
| 2010/0093828 A1 | 4/2010 | Koya et al. |
| 2010/0249239 A1 | 9/2010 | Lunsmann et al. |
| 2010/0280075 A1 | 11/2010 | Koya et al. |
| 2010/0324143 A1 | 12/2010 | Koya et al. |
| 2011/0098476 A1 | 4/2011 | Chen et al. |
| 2011/0196025 A1 | 8/2011 | Kostik et al. |
| 2011/0245262 A1 | 10/2011 | Sun et al. |
| 2011/0245577 A1 | 10/2011 | Koya |
| 2011/0288162 A1 | 11/2011 | Masazumi et al. |
| 2011/0294814 A1 | 12/2011 | Kowalczyk-Prezewloka et al. |
| 2011/0294877 A1 | 12/2011 | Masazumi et al. |
| 2011/0294895 A1 | 12/2011 | Lunsmann et al. |
| 2012/0035266 A1 | 2/2012 | Koya et al. |
| 2012/0065206 A1 | 3/2012 | Jiang et al. |
| 2012/0065235 A1 | 3/2012 | Sun et al. |

FOREIGN PATENT DOCUMENTS

JP   52-15549 A   8/1993

OTHER PUBLICATIONS

M. Mohan et al., Synthesis, Characterization and Antitumor Properties of Some Metal Complexes of 2,6-Diacetylpyridine Bis(N4-azacyclic Thiosemicarbazones), J. Inorganic Biochem. 34, 41-54 (1998).

(Continued)

*Primary Examiner* — John Mabry
(74) *Attorney, Agent, or Firm* — McCarter & English, LLP; Steven G. Davis

(57) ABSTRACT

Disclosed herein are methods of preparing a bis(thio-hydrazide amides) compounds of the following structural formula: wherein $R_1$, $R_2$, $R_3$, $R_4$, $R_5$, $R_6$ and $R_{13}$ are defined herein.

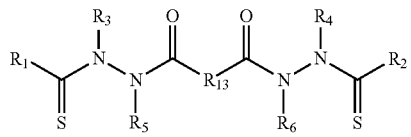

15 Claims, No Drawings

(56) References Cited

OTHER PUBLICATIONS

G. F. de Sousa et al., "Structural and Spectral Studies of a Heterocyclic N(4)-Substituted Bis(thiosemicarbazone), H22,6Achexim.H20, Its Heptacoordinated Tin(IV) Complex [Bu2Sn(2,6Achexim)], and its Binuclear Zinc(II) Complex [Zn(2,6Achexim)]2", Polyhedron, 19, 841-847 (2000).

Yusupov, V.G. et al., "Copper(II) Complexes with Benzoyl-, thiobenzoylhydrazones and thiosemicarbazones of diacetyl and 1,1-diacetylcyclopropane", Koordinatsionnaya Khimiya 16(10), 1350-1354 (1990) (English abstract only).

PROCESS FOR PREPARING BIS(THIOHYDRAZIDE AMIDES)

RELATED APPLICATIONS

This application is the U.S. National Stage of PCT International Application Number PCT/US2009/001996, filed Mar. 31, 2009, which claims the benefit of U.S. Provisional Application No. 61/072,466, filed on Mar. 31, 2008. The entire teachings of the above application(s) are incorporated herein by reference.

BACKGROUND OF THE INVENTION

It has been reported in U.S. Pat. Nos. 6,800,660, 6,762,204, 7,037,940, 7,001,923, and 6,924,312 that certain bis(thiohydrazide amide) compounds significantly enhance the anticancer activity of taxol and taxol analogs. In addition, methods of preparing bis(thio-hydrazide amide) compounds have been reported in U.S. Pat. No. 6,825,235. The entire teachings of these patents are incorporated by reference herein. Moreover, the bis(thio-hydrazide amide), N-malonyl-bis(N'-methyl-N'-thiobenzoylhydrazide), in combination with Taxol has been shown to increase the time to progress of patients suffering from stage 1V metastatic melanoma in relation to patients treated with Taxol alone. However, the synthesis of bis(thio-hydrazide amide) compounds has been complicated by the formation of regioisomers, and the effective administration of N-malonyl-bis(N'-methyl-N'-thiobenzoylhydrazide) has been challenging due to low solubility of the compound. Therefore, it would be advantageous to have new methods of preparing bis(thio-hydrazide amide) compounds.

SUMMARY OF THE INVENTION

In one embodiment, the invention relates to a method of preparing a bis(thio-hydrazide amide) represented by formula (I):

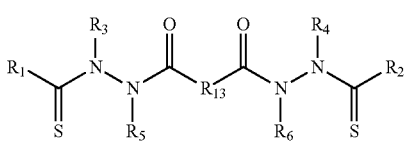

(I)

or a tautomer, pharmaceutically acceptable salt, or prodrug thereof, wherein:

$R_{13}$ is a covalent bond, or a substituted or unsubstituted C1-C6 alkylene group;

$R_1$ and $R_2$ are independently an optionally substituted aryl or an optionally substituted heteroaryl;

$R_3$ and $R_4$ are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl or an optionally substituted heteroaryl;

$R_5$ and $R_6$ are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl or an optionally substituted heteroaryl;

$R_{40}$ is an optionally substituted aryl or an optionally substituted heteroaryl;

$R_{41}$ is —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl or an optionally substituted heteroaryl;

p is 1 or 2, comprising the steps of
a) reacting a compound of formula (V):

(V)

with $S_8$, DMF and a compound of formula (VI):

(VI)

b) deprotecting the resulting compound; and
c) coupling the compound to obtain a compound of formula (I).

In one embodiment, the invention relates to a method of preparing a bis(thio-hydrazide amide) represented by formula (II):

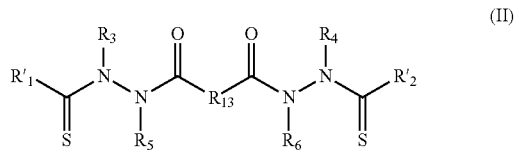

(II)

or a tautomer, pharmaceutically acceptable salt, or prodrug thereof, wherein:

$R_{13}$ is a covalent bond, or a substituted or unsubstituted C1-C6 alkylene group;

$R'_1$ and $R'_2$ are independently an optionally substituted alkyl, an optionally substituted alkenyl, an optionally substituted alkynyl, an optionally substituted cycloalkyl, an optionally substituted cycloalkenyl, or an optionally substituted heterocyclyl;

$R_3$ and $R_4$ are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl or an optionally substituted heteroaryl;

$R_5$ and $R_6$ are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl or an optionally substituted heteroaryl;

$R'_{40}$ is an optionally substituted alkyl, an optionally substituted alkenyl, an optionally substituted alkynyl, an optionally substituted cycloalkyl, an optionally substituted cycloalkenyl, or an optionally substituted heterocyclyl; and $R_{41}$ is —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl or an optionally substituted heteroaryl; comprising a) reacting a compound of formula (VII):

(VII)

with $S_8$, DMF and a compound of formula (VI):

(VI)

b) deprotecting the resulting compound; and
c) coupling the compound to obtain a compound of formula (II).

DETAILED DESCRIPTION OF THE INVENTION

The present invention relates to methods of preparing bis(thio-hydrazide amides).

In one embodiment, the invention relates to a method of preparing a bis(thio-hydrazide amide) represented by formula (I):

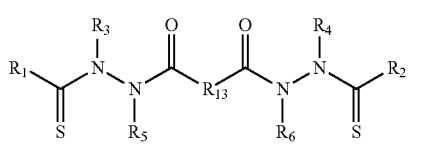

(I)

or a tautomer, pharmaceutically acceptable salt, or prodrug thereof, wherein:

$R_{13}$ is a covalent bond, or a substituted or unsubstituted C1-C6 alkylene group;

$R_1$ and $R_2$ are independently an optionally substituted aryl or an optionally substituted heteroaryl;

$R_3$ and $R_4$ are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl or an optionally substituted heteroaryl;

$R_5$ and $R_6$ are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl or an optionally substituted heteroaryl;

$R_{40}$ is an optionally substituted aryl or an optionally substituted heteroaryl;

$R_{41}$ is —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl or an optionally substituted heteroaryl;

p is 1 or 2, comprising the steps of
a) reacting a compound of formula (V):

(V)

with $S_8$, DMF and a compound of formula (VI):

(VI)

b) deprotecting the resulting compound to form a deprotected compound; and
c) coupling the deprotected compound to obtain a compound of formula (I).

In one embodiment, the invention relates to a method of preparing a bis(thio-hydrazide amide) represented by formula (II):

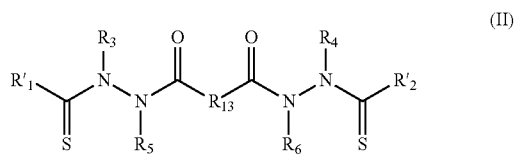

(II)

or a tautomer, pharmaceutically acceptable salt, or prodrug thereof, wherein:

$R_{13}$ is a covalent bond, or a substituted or unsubstituted C1-C6 alkylene group;

$R'_1$ and $R'_2$ are independently an optionally substituted alkyl, an optionally substituted alkenyl, an optionally substituted alkynyl, an optionally substituted cycloalkyl, an optionally substituted cycloalkenyl, or an optionally substituted heterocyclyl;

$R_3$ and $R_4$ are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl or an optionally substituted heteroaryl;

$R_5$ and $R_6$ are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl or an optionally substituted heteroaryl;

$R'_{40}$ is an optionally substituted alkyl, an optionally substituted alkenyl, an optionally substituted alkynyl, an optionally substituted cycloalkyl, an optionally substituted cycloalkenyl, or an optionally substituted heterocyclyl; and $R_{41}$ is —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl or an optionally substituted heteroaryl; comprising a) reacting a compound of formula (VII):

with $S_8$, DMF and a compound of formula (VI):

b) deprotecting the resulting compound to form a deprotected compound; and c) coupling the deprotected compound to obtain a compound of formula (II).

As used herein, "coupling" includes, for example, reacting the deprotected compound with a carboxylic acid or a carboxylic acid derivative. Typically, the carboxylic acid is first converted into a carboxylic derivative with a group that is more readily displaced by an amine or hydrazine than —OH. Thus, —OH is converted into a better leaving group. A "leaving group" is a group which can readily be displaced by a nucleophile.

In one example, —OH of the carboxylic acid is converted into a better leaving group by replacing it with a halogen, typically with chloride. The carboxylic acid is thereby converted into an acid halide, e.g., an acid chloride. Reagents suitable for preparing acid chlorides from carboxylic acids are well known in the art and include thionyl chloride, oxalyl chloride, phosphorus trichloride and phosphorus pentachloride. Typically, each carboxylic acid group is reacted with about one equivalent or a slight excess of thionyl chloride, oxalyl chloride, phosphorus trichloride and phosphorus pentachloride in an inert solvent such as an ethereal solvent (e.g., diethyl ether, tetrahydrofuran or 1,4-dioxane), a halogenated solvent (e.g., methylene chloride or 1,2-dichloroethane) or aromatic solvent (e.g., benzene or toluene). When oxalyl chloride is used, a tertiary amine is often added to accelerate the reaction in quantities ranging from a catalytic amount to about one equivalent relative to oxalyl chloride.

Alternatively, the carboxylic acid is first converted into an "activated ester". An ester —COOR is said to be "activated" when —OR is readily displaced by an amine or hydrazine. —OR is more easily displaced as R becomes more electron withdrawing. Some activated esters are sufficiently stable that they can be isolated, e.g., esters wherein R is phenyl or substituted phenyl. For example, diphenylmalonate can be prepared from malonyl chloride and phenol, both commercially available from Aldrich Chemical Co., Milwaukee, Wis., by procedures described above Other activated esters are more reactive and are generally prepared and used in situ.

Formation of an activated ester in situ requires a "coupling agent", also referred to as a "carboxylic acid activating agent", which is a reagent that replaces the hydroxyl group of a carboxyl acid with a group which is susceptible to nucleophilic displacement. Examples of coupling agents include 1,1'-carbonyldiimidazole (CDI), isobutyl chloroformate, dimethylaminopropylethyl-carbodiimide (EDC), dicyclohexyl carbodiimide (DCC). When amidating by in situ generation of an activated ester, an excess of either the carboxylic acid or hydrazine can be used (typically a 50% excess, more typically about a 10-15% excess). However, it is more common when carrying out the present invention to use the hydrazine compound as the limiting reagent. Generally, from about 1.0 equivalent to about 10 equivalents of coupling agent are used relative to each carboxylic acid group, preferably from about 1.0 equivalent to about 1.5 equivalents. When DCC is used, a weak acid such as 1-hydroxybenzotriazole (HOBt) is often added to accelerate the reaction. Typically, about between one to about 1.5 equivalents of HOBt relative to DCC is used, preferably between about one to about 1.2 equivalents. The reaction is generally carried out in inert, aprotic solvents, for example, halogenated solvents such as methylene chloride, dichloroethane and chloroform, ethereal solvents such as tetrahydrofuran, 1,4-dioxane and diethyl ether and dimethylformamide. Suitable reaction temperature generally range from between about 0° to about 100°, but the reaction is preferably carried out at ambient temperature. Representative conditions for carrying out these reactions are found in Examples 1-9.

In one embodiment, "coupling the deprotected compound" refers to reacting the deprotected compound with Z—C(O)—$R_{13}$—(CO)—Z or HO—C(O)—$R_{13}$—(CO)—OH and a carboxylic acid activating agent, wherein each Z is a leaving group. In a more specific embodiment, Z is —Cl or —OR, wherein R is phenyl or a phenyl with at least one electron-withdrawing group, such as —$NO_2$.

In another embodiment, "coupling the deprotected compound" refers to reacting the deprotected compound with Z—(O)C—Y—$COOR_6$ or with HO—(O)C—Y—$COOR_6$ and a carboxylic acid activating group, wherein $R_6$ is a carboxylic acid protecting group, Z is a leaving group. Suitable protecting groups for carboxylic acids and conditions for protecting and deprotecting carboxylic acids with these groups are known in the art and are described, for example, in Greene and Wuts, "Protective Groups in Organic Synthesis", John Wiley & Sons (1991). The entire teachings of Greene and Wits are incorporated herein by reference. Specific examples of suitable carboxylic acid protecting groups for Structural Formula (V) include, but are not limited to tert-butoxy, benzoxy, phenoxy, diphenylmethoxy, triphenylmethoxy and methoxymethyl.

In another embodiment, the bis(thio-hydrazide amide) is represented by formula (III):

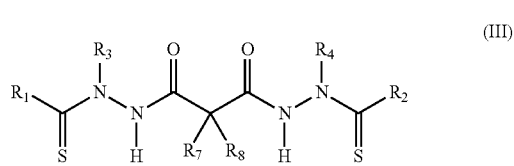

or a tautomer, pharmaceutically acceptable salt, or prodrug thereof, wherein:

$R_7$ and $R_8$ are each independently —H or an optionally substituted alkyl, an optionally substituted alkenyl, an optionally substituted alkynyl, an optionally substituted cycloalkyl, an optionally substituted cycloalkenyl, an optionally substituted heterocyclyl, or $R_7$ is —H and $R_8$ is an optionally substituted aryl or an optionally substituted heteroaryl; and $R_1$, $R_2$, $R_3$, $R_4$, $R_5$, and $R_6$, are defined as for formula (I).

In another embodiment, the bis(thio-hydrazide amide) is represented by formula (IV):

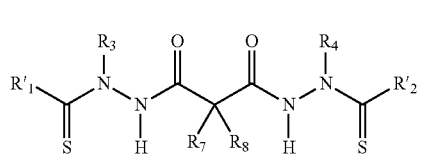

or a tautomer, pharmaceutically acceptable salt, or prodrug thereof, wherein:

$R_7$ and $R_8$ are each independently —H or an optionally substituted alkyl, an optionally substituted alkenyl, an optionally substituted alkynyl, an optionally substituted cycloalkyl, an optionally substituted cycloalkenyl, an optionally substituted heterocyclyl, or $R_7$ is —H and $R_8$ is an optionally substituted aryl or an optionally substituted heteroaryl; and $R'_1$, $R'_2$, $R_3$, $R_4$, $R_5$, and $R_6$, are defined as for formula (II).

Another embodiment of the invention is a method of preparing a compound represented by formula (VIII):

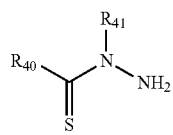

wherein:

$R_{40}$ is an optionally substituted aryl or an optionally substituted heteroaryl; and $R_{41}$ is —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl or an optionally substituted heteroaryl; comprising a) reacting a compound of formula (V):

with $S_8$, DMF and a compound of formula (VI):

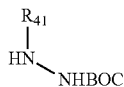

b) and, deprotecting the resulting compound.

Another embodiment of the invention is a method of preparing a compound represented by formula (IX):

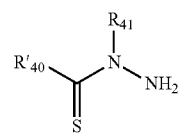

wherein:

$R'_{40}$ is an optionally substituted alkyl, an optionally substituted alkenyl, an optionally substituted alkynyl, an optionally substituted cycloalkyl, an optionally substituted cycloalkenyl, or an optionally substituted heterocyclyl; and $R_{41}$ is —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl or an optionally substituted heteroaryl; comprising a) reacting a compound of formula (VII):

with $S_8$, DMF and a compound of formula (VI):

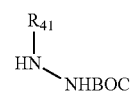

b) and, deprotecting the resulting compound.

In another embodiment, the bis(thio-hydrazide amide) is N-malonyl-bis(N'-methyl-N'-thiobenzoylhydrazide) represented by the following structural formula:

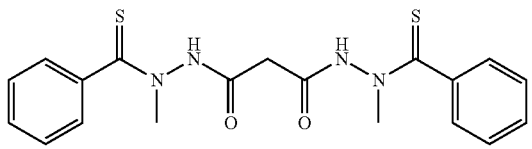 [SMILES: CN(NC(=O)CC(=O)NN(C)C(=S)c1ccccc1)C(=S)c1ccccc1]

or a tautomer, pharmaceutically acceptable salt, or prodrug thereof.

In one embodiment of the compounds of formula (I) or (III), $R_1$ and $R_2$ are each an optionally substituted aryl or an optionally substituted heteroaryl. In one aspect, $R_1$ and $R_2$ are each a substituted or unsubstituted phenyl group. In one aspect, $R_1$ and $R_2$ are each an optionally substituted pyridyl. In another aspect, $R_1$ and $R_2$ are each 4-cyanophenyl, 4-methoxyphenyl, 2,5-dimethoxyphenyl, 3-cyanophenyl, 3-fluorophenyl, 4-chlorophenyl, 2-dimethoxyphenyl, 3-methoxyphenyl, 2,3-dimethoxyphenyl, 2,5-difluorophenyl, 2,5-dichlorophenyl, or 2,5-dimethylphenyl. In another aspect, $R_1$ and $R_2$ are both 4-cyanophenyl. In another aspect, $R_1$ and $R_2$ are both 4-methoxyphenyl. In a further aspect, $R_1$ and $R_2$ are both 2,5-dimethoxyphenyl. In another aspect, $R_1$ and $R_2$ are both 3-cyanophenyl. In one aspect, $R_1$ and $R_2$ are both 3-fluorophenyl. In another aspect, $R_1$ and $R_2$ are both 4-chlorophenyl. In one aspect, $R_1$ and $R_2$ are both 2-dimethoxyphenyl. In another aspect, $R_1$ and $R_2$ are both 3-methoxyphenyl. In one aspect, $R_1$ and $R_2$ are both 2,3-dimethoxyphenyl. In another aspect, $R_1$ and $R_2$ are both 2,5-difluorophenyl. In one aspect, $R_1$ and $R_2$ are both 2,5-difluorophenyl. In another aspect, $R_1$ and $R_2$ are both 2,5-dichlorophenyl. In one aspect, $R_1$ and $R_2$ are both 2,5-dimethylphenyl.

In one embodiment of the compounds of formula (II) or (IV), $R'_1$ and $R'_2$ are both an optionally substituted alkyl, an optionally substituted alkenyl, an optionally substituted alkynyl, an optionally substituted cycloalkyl, an optionally substituted cycloalkenyl, an optionally substituted heterocyclyl. In one aspect, $R'_1$ and $R'_2$ are both a C3-C8 cycloalkyl group optionally substituted with at least one alkyl group. In a further aspect, $R'_1$ and $R'_2$ are both cyclopropyl, 1-methylcyclopropyl, 2-phenylcyclopropyl, 2-methylcyclopropyl, 1-phenylcyclopropyl, cyclobutyl, cyclopentyl, cyclohexyl, methyl, ethyl, n-propyl, or t-butyl. In another aspect, $R'_1$ and $R'_2$ are both cyclopropyl or 1-methylcyclopropyl. In one aspect, $R'_1$ and $R'_2$ are both 2-phenylcyclopropyl. In another aspect, $R'_1$ and $R'_2$ are both 2-methylcyclopropyl. In another aspect, $R'_1$ and $R'_2$ are both 1-phenylcyclopropyl. In one aspect, $R'_1$ and $R'_2$ are both cyclobutyl. In another aspect, $R'_1$ and $R'_2$ are both cyclopentyl. In one aspect, $R'_1$ and $R'_2$ are both cyclohexyl. In a further aspect, $R'_1$ and $R'_2$ are both methyl. In another aspect, $R'_1$ and $R'_2$ are both t-butyl. In one aspect, $R'_1$ and $R'_2$ are ethyl. In another aspect, $R'_1$ and $R'_2$ are both n-propyl.

In one embodiment of the compounds of formula (I), (II), (III), or (IV), $R_3$ and $R_4$ are each an optionally substituted alkyl, an optionally substituted alkenyl, an optionally substituted alkynyl, an optionally substituted cycloalkyl, an optionally substituted cycloalkenyl, an optionally substituted heterocyclyl. In one aspect, $R_3$ and $R_4$ are each an alkyl group. In another aspect, $R_3$ and $R_4$ are each methyl or ethyl. In one aspect, $R_3$ and $R_4$ are both methyl. In another aspect, $R_3$ and $R_4$ are both ethyl. In a further aspect, $R_3$ and $R_4$ are both t-butyl.

In one embodiment of the compounds of formula (I), (II), (III), or (IV), $R_3$ and $R_4$ are both phenyl.

In one embodiment of the compounds of formula (I) or (II), $R_5$ is —H and $R_6$ is —H, an optionally substituted alkyl, an optionally substituted alkenyl, an optionally substituted alkynyl, an optionally substituted cycloalkyl, an optionally substituted cycloalkenyl, or an optionally substituted heterocyclyl. In one aspect, $R_6$ is —H or methyl. In one aspect, $R_5$ and $R_6$ are both —H.

In one embodiment of the compounds of formula (I) or (II), $R_{13}$ is a covalent bond.

In one embodiment of the compounds of formula (I) or (II), $R_{13}$ is —$CH_2CH_2CH_2$— or —$CH_2CH_2$.

In one embodiment of the compounds of formula (I) or (II), $R_{13}$ is —$C(R_7)(R_8)$—; $R_7$ and $R_8$ are each independently —H or an optionally substituted alkyl, an optionally substituted alkenyl, an optionally substituted alkynyl, an optionally substituted cycloalkyl, an optionally substituted cycloalkenyl, an optionally substituted heterocyclyl, or $R_7$ is —H and $R_8$ is an optionally substituted aryl or an optionally substituted heteroaryl.

In one embodiment of the compounds of formula (I), $R_1$ and $R_2$ are each an optionally substituted aryl or an optionally substituted heteroaryl; and $R_3$ and $R_4$ are each an optionally substituted alkyl, an optionally substituted alkenyl, an optionally substituted alkynyl, an optionally substituted cycloalkyl, an optionally substituted cycloalkenyl, an optionally substituted heterocyclyl. In one aspect, $R_5$ is —H and $R_6$ is —H, an optionally substituted alkyl, an optionally substituted alkenyl, an optionally substituted alkynyl, an optionally substituted cycloalkyl, an optionally substituted cycloalkenyl, an optionally substituted heterocyclyl; and $R_3$ and $R_4$ are each an alkyl group. In another aspect, $R_1$ and $R_2$ are each a substituted or unsubstituted phenyl group and $R_3$ and $R_4$ are each methyl or ethyl.

In one embodiment of the compounds of formula (II), $R'_1$ and $R'_2$ are both an optionally substituted alkyl, an optionally substituted alkenyl, an optionally substituted alkynyl, an optionally substituted cycloalkyl, an optionally substituted cycloalkenyl, an optionally substituted heterocyclyl; $R_5$ is —H; and $R_6$ is —H or an optionally substituted alkyl, an optionally substituted alkenyl, an optionally substituted alkynyl, an optionally substituted cycloalkyl, an optionally substituted cycloalkenyl, an optionally substituted heterocyclyl. In one aspect, $R'_1$ and $R'_2$ are both a C3-C8 cycloalkyl group optionally substituted with at least one alkyl group; $R_3$ and $R_4$ are both an alkyl group; and $R_6$ is —H or methyl. In another aspect, $R'_1$ and $R'_2$ are both cyclopropyl or 1-methylcyclopropyl.

In one embodiment of the compounds of formula (III), $R_1$ and $R_2$ are both phenyl; $R_3$ and $R_4$ are both methyl; $R_7$ and $R_8$ are both —H;

$R_1$ and $R_2$ are both phenyl; $R_3$ and $R_4$ are both ethyl; $R_7$ and $R_8$ are both —H;

$R_1$ and $R_2$ are both 4-cyanophenyl; $R_3$ and $R_4$ are both methyl; $R_7$ is methyl; $R_8$ is —H;

$R_1$ and $R_2$ are both 4-methoxyphenyl; $R_3$ and $R_4$ are both methyl; $R_7$ and $R_8$ are both —H;

$R_1$ and $R_2$ are both phenyl; $R_3$ and $R_4$ are both methyl; $R_7$ is methyl; $R_8$ is —H;

$R_1$ and $R_2$ are both phenyl; $R_3$ and $R_4$ are both ethyl; $R_7$ is methyl; $R_8$ is —H;

$R_1$ and $R_2$ are both 4-cyanophenyl; $R_3$ and $R_4$ are both methyl; $R_7$ and $R_8$ are both —H;

$R_1$ and $R_2$ are both 2,5-dimethoxyphenyl; $R_3$ and $R_4$ are both methyl; $R_7$ and $R_8$ are both —H;

$R_1$ and $R_2$ are both 2,5-dimethoxyphenyl; $R_3$ and $R_4$ are both methyl; $R_7$ is methyl; $R_8$ is —H;

$R_1$ and $R_2$ are both 3-cyanophenyl; $R_3$ and $R_4$ are both methyl; $R_7$ and $R_8$ are both —H;

$R_1$ and $R_2$ are both 3-fluorophenyl; $R_3$ and $R_4$ are both methyl; $R_7$ and $R_8$ are both —H;

$R_1$ and $R_2$ are both 4-chlorophenyl; $R_3$ and $R_4$ are both methyl; $R_7$ is methyl; $R_8$ is —H;

$R_1$ and $R_2$ are both 2-dimethoxyphenyl; $R_3$ and $R_4$ are both methyl; $R_7$ and $R_8$ are both —H;

$R_1$ and $R_2$ are both 3-methoxyphenyl; $R_3$ and $R_4$ are both methyl; $R_7$ and $R_8$ are both —H;

$R_1$ and $R_2$ are both 2,3-dimethoxyphenyl; $R_3$ and $R_4$ are both methyl; $R_7$ and $R_8$ are both —H;

$R_1$ and $R_2$ are both 2,3-dimethoxyphenyl; $R_3$ and $R_4$ are both methyl; $R_7$ is methyl; $R_8$ is —H;

$R_1$ and $R_2$ are both 2,5-difluorophenyl; $R_3$ and $R_4$ are both methyl; $R_7$ and $R_8$ are both —H;

$R_1$ and $R_2$ are both 2,5-difluorophenyl; $R_3$ and $R_4$ are both methyl; $R_7$ is methyl; $R_8$ is —H;

$R_1$ and $R_2$ are both 2,5-dichlorophenyl; $R_3$ and $R_4$ are both methyl; $R_7$ and $R_8$ are both —H;

$R_1$ and $R_2$ are both 2,5-dimethylphenyl; $R_3$ and $R_4$ are both methyl; $R_7$ and $R_8$ are both —H;

$R_1$ and $R_2$ are both 2,5-dimethoxyphenyl; $R_3$ and $R_4$ are both methyl; $R_7$ and $R_8$ are both —H;

$R_1$ and $R_2$ are both phenyl; $R_3$ and $R_4$ are both methyl; $R_7$ and $R_8$ are both —H; or $R_1$ and $R_2$ are both 2,5-dimethoxyphenyl; $R_3$ and $R_4$ are both methyl; $R_7$ is methyl; $R_8$ is —H;

In one embodiment of the compounds of formula (IV), $R'_1$ and $R'_2$ are both cyclopropyl; $R_3$ and $R_4$ are both methyl; $R_7$ and $R_8$ are both —H;

$R'_1$ and $R'_2$ are both cyclopropyl; $R_3$ and $R_4$ are both ethyl; $R_7$ and $R_8$ are both —H;

$R'_1$ and $R'_2$ are both cyclopropyl; $R_3$ and $R_4$ are both methyl; $R_7$ is methyl; $R_8$ is —H;

$R'_1$ and $R'_2$ are both 1-methylcyclopropyl; $R_3$ and $R_4$ are both methyl; $R_7$ and $R_8$ are both —H;

$R'_1$ and $R'_2$ are both 1-methylcyclopropyl; $R_3$ and $R_4$ are both methyl; $R_7$ is methyl and $R_8$ is —H;

$R'_1$ and $R'_2$ are both 1-methylcyclopropyl; $R_3$ and $R_4$ are both methyl; $R_7$ is ethyl and $R_8$ is —H;

$R'_1$ and $R'_2$ are both 1-methylcyclopropyl; $R_3$ and $R_4$ are both methyl; $R_7$ is n-propyl and $R_8$ is —H;

$R'_1$ and $R'_2$ are both 1-methylcyclopropyl; $R_3$ and $R_4$ are both methyl; $R_7$ and $R_8$ are both methyl;

$R'_1$ and $R'_2$ are both 1-methylcyclopropyl; $R_3$ and $R_4$ are both ethyl; $R_7$ and $R_8$ are both —H;

$R'_1$ and $R'_2$ are both 1-methylcyclopropyl; $R_3$ is methyl, and $R_4$ is ethyl; $R_7$ and $R_8$ are both —H;

$R'_1$ and $R'_2$ are both 2-methylcyclopropyl; $R_3$ and $R_4$ are both methyl; $R_7$ and $R_8$ are both —H;

$R'_1$ and $R'_2$ are both 2-phenylcyclopropyl; $R_3$ and $R_4$ are both methyl; $R_7$ and $R_8$ are both —H;

$R'_1$ and $R'_2$ are both 1-phenylcyclopropyl; $R_3$ and $R_4$ are both methyl; $R_7$ and $R_8$ are both —H;

$R'_1$ and $R'_2$ are both cyclobutyl; $R_3$ and $R_4$ are both methyl; $R_7$ and $R_8$ are both —H;

$R'_1$ and $R'_2$ are both cyclopentyl; $R_3$ and $R_4$ are both methyl; $R_7$ and $R_8$ are both —H;

$R'_1$ and $R'_2$ are both cyclohexyl; $R_3$ and $R_4$ are both methyl; $R_7$ and $R_8$ are both —H;

$R'_1$ and $R'_2$ are both cyclohexyl; $R_3$ and $R_4$ are both phenyl; $R_7$ and $R_8$ are both —H;

$R'_1$ and $R'_2$ are both methyl; $R_3$ and $R_4$ are both methyl; $R_7$ and $R_8$ are both —H;

$R'_1$ and $R'_2$ are both methyl; $R_3$ and $R_4$ are both t-butyl; $R_7$ and $R_8$ are both —H;

$R'_1$ and $R'_2$ are both methyl; $R_3$ and $R_4$ are both phenyl; $R_7$ and $R_8$ are both —H;

$R'_1$ and $R'_2$ are both t-butyl; $R_3$ and $R_4$ are both methyl; $R_7$ and $R_8$ are both —H;

$R'_1$ and $R'_2$ are ethyl; $R_3$ and $R_4$ are both methyl; $R_7$ and $R_8$ are both —H; or $R'_1$ and $R'_2$ are both n-propyl; $R_3$ and $R_4$ are both methyl; $R_7$ and $R_8$ are both —H.

In one embodiment of the compounds of formula (V) or (VIII), $R_{40}$ is an optionally substituted aryl or an optionally substituted heteroaryl. In one aspect, $R_{40}$ is a substituted or unsubstituted phenyl group. In one aspect, $R_{40}$ is an optionally substituted pyridyl. In another aspect, $R_{40}$ is 4-cyanophenyl, 4-methoxyphenyl, 2,5-dimethoxyphenyl, 3-cyanophenyl, 3-fluorophenyl, 4-chlorophenyl, 2-dimethoxyphenyl, 3-methoxyphenyl, 2,3-dimethoxyphenyl, 2,5-difluorophenyl, 2,5-dichlorophenyl, or 2,5-dimethylphenyl. In another aspect, $R_{40}$ is 4-cyanophenyl. In another aspect, $R_{40}$ is 4-methoxyphenyl. In a further aspect, $R_{40}$ is 2,5-dimethoxyphenyl. In another aspect, $R_{40}$ is 3-cyanophenyl. In one aspect, $R_{40}$ is 3-fluorophenyl. In another aspect, $R_{40}$ is 4-chlorophenyl. In one aspect, $R_{40}$ is 2-dimethoxyphenyl. In another aspect, $R_{40}$ is 3-methoxyphenyl. In one aspect, $R_{40}$ is 2,3-dimethoxyphenyl. In another aspect, $R_{40}$ is 2,5-difluorophenyl. In one aspect, $R_{40}$ is 2,5-difluorophenyl. In another aspect, $R_{40}$ is 2,5-dichlorophenyl. In one aspect, $R_{40}$ is 2,5-dimethylphenyl.

In one embodiment of the compounds of formula (VII) or (IX), $R'_{40}$ is an optionally substituted aryl or an optionally substituted heteroaryl. In one aspect, $R'_{40}$ is a substituted or unsubstituted phenyl group. In one aspect, $R'_{40}$ is an optionally substituted pyridyl. In another aspect, $R'_{40}$ is 4-cyanophenyl, 4-methoxyphenyl, 2,5-dimethoxyphenyl, 3-cyanophenyl, 3-fluorophenyl, 4-chlorophenyl, 2-dimethoxyphenyl, 3-methoxyphenyl, 2,3-dimethoxyphenyl, 2,5-difluorophenyl, 2,5-dichlorophenyl, or 2,5-dimethylphenyl. In another aspect, $R'_{40}$ is 4-cyanophenyl. In another aspect, $R'_{40}$ is 4-methoxyphenyl. In a further aspect, $R'_{40}$ is 2,5-dimethoxyphenyl. In another aspect, $R'_{40}$ is 3-cyanophenyl. In one aspect, $R'_{40}$ is 3-fluorophenyl. In another aspect, $R'_{40}$ is 4-chlorophenyl. In one aspect, $R'_{40}$ is 2-dimethoxyphenyl. In another aspect, $R'_{40}$ is 3-methoxyphenyl. In one aspect, $R'_{40}$ is 2,3-dimethoxyphenyl. In another aspect, $R'_{40}$ is 2,5-difluorophenyl. In one aspect, $R'_{40}$ is 2,5-difluorophenyl. In another aspect, $R'_{40}$ is 2,5-dichlorophenyl. In one aspect, $R'_{40}$ is 2,5-dimethylphenyl.

In one embodiment of the compounds of formula (VI), (VIII), or (IX), $R_{41}$ is an optionally substituted alkyl, an optionally substituted alkenyl, an optionally substituted alkynyl, an optionally substituted cycloalkyl, an optionally substituted cycloalkenyl, an optionally substituted heterocyclyl. In one aspect, $R_{41}$ is an alkyl group. In another aspect, $R_{41}$ is methyl or ethyl. In one aspect, $R_{41}$ is methyl. In another aspect, $R_{41}$ is ethyl. In a further aspect, $R_{41}$ is t-butyl.

In one embodiment of the compound of formula (VIII) is

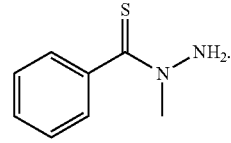

In one embodiment of the compound of formula (VIII) is

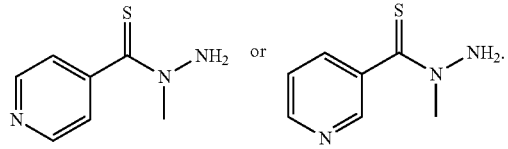

Preferred examples of bis(thio-hydrazide amides) include Compounds (1)-(18) and pharmaceutically acceptable salts or prodrugs thereof:

Compound (1)

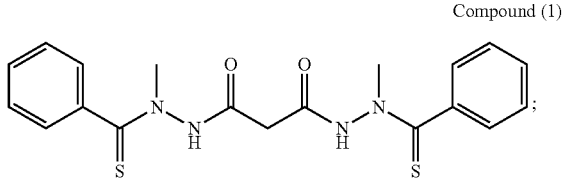

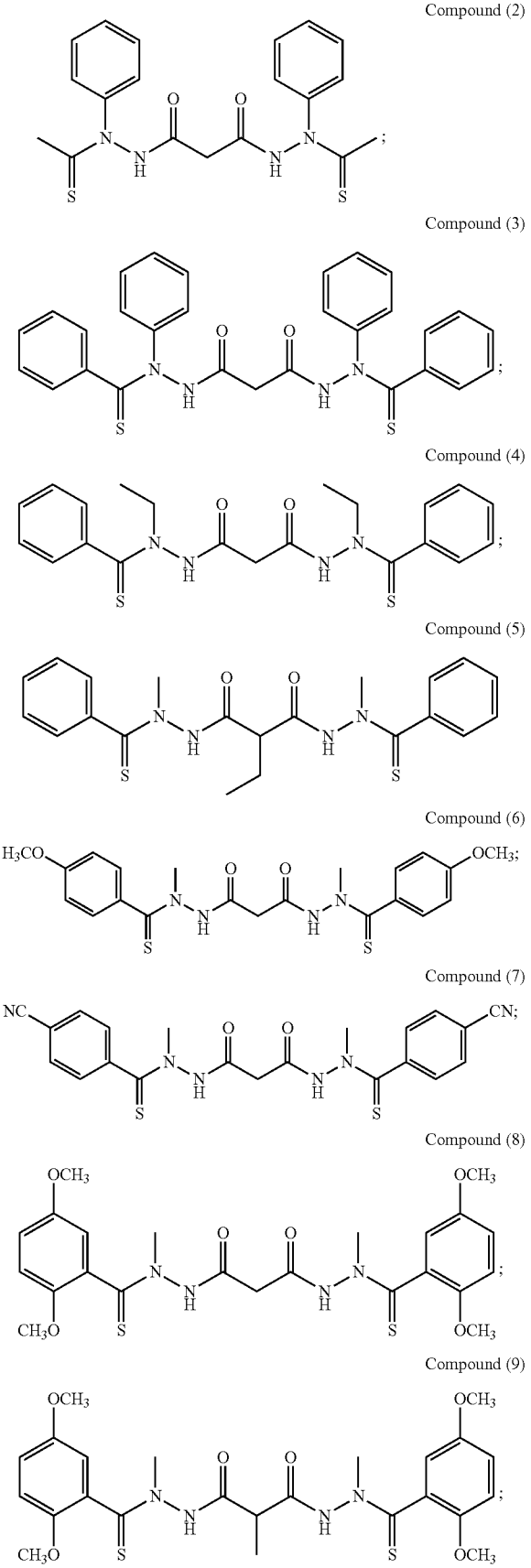
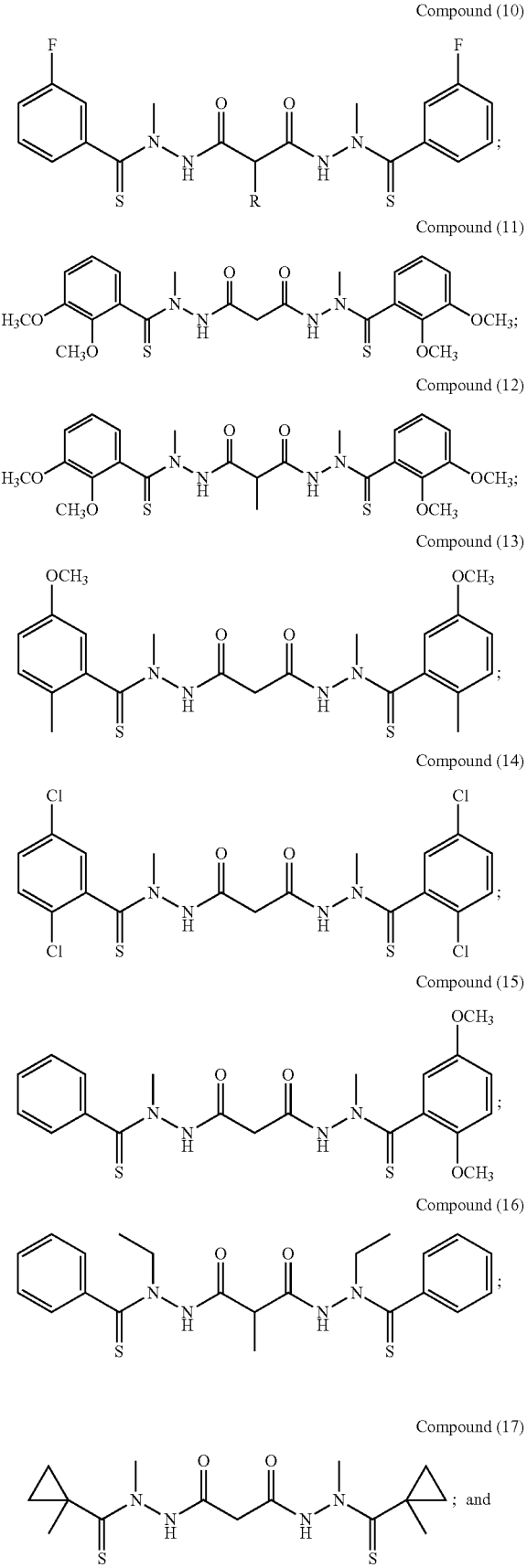

-continued

Compound (18)

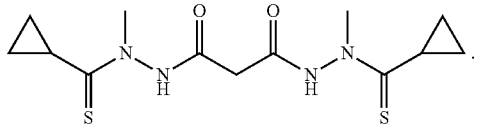

As used herein, the term "bis(thio-hydrazide amide)" and references to the Structural Formulas of this invention also include pharmaceutically acceptable salts and solvates of these compounds and Structural Formulas. Examples of acceptable salts and solvates are described in US Publication No.: 20060135595 and U.S. patent application Ser. No. 11/432,307 filed 11 May 2006, titled Synthesis Of Bis(Thio-Hydrazide Amide) Salts, the entire contents of each of which are incorporated herein by reference.

It is to be understood when one tautomeric form of a disclosed compound is depicted structurally, other tautomeric forms are also encompassed.

Certain compounds of the invention may be obtained as different stereoisomers (e.g., diastereomers and enantiomers). The invention includes all isomeric forms and racemic mixtures of the disclosed compounds and methods of treating a subject with both pure isomers and mixtures thereof, including racemic mixtures. Stereoisomers can be separated and isolated using any suitable method, such as chromatography.

As used herein, the term "alkyl" means a saturated straight chain or branched non-cyclic hydrocarbon having from 1 to 10 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. The term "($C_1$-$C_6$)alkyl" means a saturated straight chain or branched non-cyclic hydrocarbon having from 1 to 6 carbon atoms. Representative ($C_1$-$C_6$)alkyl groups are those shown above having from 1 to 6 carbon atoms. Alkyl groups included in compounds of this invention may be optionally substituted with one or more substituents.

As used herein, the term "alkenyl" means a saturated straight chain or branched non-cyclic hydrocarbon having from 2 to 10 carbon atoms and having at least one carbon-carbon double bond. Representative straight chain and branched ($C_2$-$C_{10}$)alkenyls include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl and the like. Alkenyl groups may be optionally substituted with one or more substituents.

As used herein, the term "alkynyl" means a saturated straight chain or branched non-cyclic hydrocarbon having from 2 to 10 carbon atoms and having at lease one carbon-carbon triple bond. Representative straight chain and branched alkynyls include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl, and the like. Alkynyl groups may be optionally substituted with one or more substituents.

As used herein, the term "cycloalkyl" means a saturated, mono- or polycyclic alkyl radical having from 3 to 20 carbon atoms. Representative cycloalkyls include cyclopropyl, 1-methylcyclopropyl, cyclobutyl, cyclopentyl, cyclohexyl, cycloheptyl, cyclooctyl, cyclononyl, -cyclodecyl, octahydropentalenyl, and the like. Cycloalkyl groups may be optionally substituted with one or more substituents.

As used herein, the term "cycloalkenyl" means a mono- or poly-cyclic non-aromatic alkyl radical having at least one carbon-carbon double bond in the cyclic system and from 3 to 20 carbon atoms. Representative cycloalkenyls include cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl, 1,2,3,4,5,8-hexahydronaphthalenyl and the like. Cycloalkenyl groups may be optionally substituted with one or more substituents.

As used herein, the term "haloalkyl" means and alkyl group in which one or more (including all) the hydrogen radicals are replaced by a halo group, wherein each halo group is independently selected from —F, —Cl, —Br, and —I. The term "halomethyl" means a methyl in which one to three hydrogen radical(s) have been replaced by a halo group. Representative haloalkyl groups include trifluoromethyl, bromomethyl, 1,2-dichloroethyl, 4-iodobutyl, 2-fluoropentyl, and the like.

As used herein, an "alkoxy" is an alkyl group which is attached to another moiety via an oxygen linker.

As used herein, a "haloalkoxy" is a haloalkyl group which is attached to another moiety via an oxygen linker.

As used herein, the term "aryl" means a hydrocarbon monocyclic or polycyclic radical in which at least one ring is aromatic. Examples of suitable aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Aryl groups may be optionally substituted with one or more substituents. In one embodiment, the aryl group is a monocyclic ring, wherein the ring comprises 6 carbon atoms, referred to herein as "($C_6$)aryl."

As used herein, the term "aralkyl" means an aryl group that is attached to another group by a ($C_1$-$C_6$)alkylene group. Representative aralkyl groups include benzyl, 2-phenylethyl, naphth-3-yl-methyl and the like. Aralkyl groups may be optionally substituted with one or more substituents.

As used herein, the term "alkylene" refers to an alkyl group that has two points of attachment. The term "($C_1$-$C_6$)alkylene" refers to an alkylene group that has from one to six carbon atoms. Straight chain ($C_1$-$C_6$)alkylene groups are preferred. Non-limiting examples of alkylene groups include methylene (—$CH_2$—), ethylene (—$CH_2CH_2$—), n-propylene (—$CH_2CH_2CH_2$—), isopropylene (—$CH_2CH$($CH_3$)—), and the like. Alkylene groups may be optionally substituted with one or more substituents.

As used herein, the term "heterocyclyl" means a monocyclic (typically having 3- to 10-members) or a polycyclic (typically having 7- to 20-members) heterocyclic ring system which is either a saturated ring or an unsaturated non-aromatic ring. A 3- to 10-membered heterocycle can contain up to 5 heteroatoms; and a 7- to 20-membered heterocycle can contain up to 7 heteroatoms. Typically, a heterocycle has at least on carbon atom ring member. Each heteroatom is independently selected from nitrogen, which can be oxidized (e.g., N(O)) or quaternized; oxygen; and sulfur, including sulfoxide and sulfone. The heterocycle may be attached via any heteroatom or carbon atom. Representative heterocycles include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. A heteroatom may be substituted with a protecting group known to those of ordinary skill in the art, for example, the hydrogen on a nitrogen may be substituted with a tert-butoxycarbonyl group. Furthermore, the heterocyclyl may be optionally substituted with one or more substituents. Only stable isomers of such substituted heterocyclic groups are contemplated in this definition.

As used herein, the term "heteroaromatic", "heteroaryl" or like terms means a monocyclic or polycyclic heteroaromatic ring comprising carbon atom ring members and one or more heteroatom ring members. Each heteroatom is independently selected from nitrogen, which can be oxidized (e.g., N(O)) or quaternized; oxygen; and sulfur, including sulfoxide and sulfone. Representative heteroaryl groups include pyridyl, 1-oxo-pyridyl, furanyl, benzo[1,3]dioxolyl, benzo[1,4]dioxinyl, thienyl, pyrrolyl, oxazolyl, imidazolyl, thiazolyl, a isoxazolyl, quinolinyl, pyrazolyl, isothiazolyl, pyridazinyl, pyrimidinyl, pyrazinyl, a triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo[1,2-a]pyridyl, and benzothienyl. In one embodiment, the heteroaromatic ring is selected from 5-8 membered monocyclic heteroaryl rings. The point of attachment of a heteroaromatic or heteroaryl ring to another group may be at either a carbon atom or a heteroatom of the heteroaromatic or heteroaryl rings. Heteroaryl groups may be optionally substituted with one or more substituents.

As used herein, the term "($C_5$)heteroaryl" means an aromatic ring of 5 members, wherein at least one atom in the ring is a heteroatom such as, for example, oxygen, sulfur or nitrogen. Representative ($C_5$)heteroaryls include furanyl, thienyl, pyrrolyl, oxazolyl, imidazolyl, thiazolyl, isoxazolyl, pyrazolyl, isothiazolyl, pyrazinyl, triazolyl, thiadiazolyl, and the like.

As used herein, the term "($C_6$)heteroaryl" means an aromatic ring of 6 members, wherein at least one atom in the ring is a heteroatom such as, for example, oxygen, nitrogen or sulfur. Representative ($C_6$)heteroaryls include pyridyl, pyridazinyl, pyrazinyl, triazinyl, tetrazinyl and the like.

As used herein, the term "heteroaralkyl" means a heteroaryl group that is attached to another group by a ($C_1$-$C_6$) alkylene. Representative heteroaralkyls include 2-(pyridin-4-yl)-propyl, 2-(thien-3-yl)-ethyl, imidazol-4-yl-methyl and the like. Heteroaralkyl groups may be optionally substituted with one or more substituents.

As used herein, the term "halogen" or "halo" means —F, —Cl, —Br or —I.

Suitable substituents for an alkyl, alkylene, alkenyl, alkynyl, cycloalkyl, cycloalkenyl, heterocyclyl, aryl, aralkyl, heteroaryl, and heteroalkyl groups include any substituent which will form a stable compound of the invention. Examples of substituents for an alkyl, alkylene, alkenyl, alkynyl, cycloalkyl, cycloalkenyl, heterocyclyl, aryl, aralkyl, heteroaryl, and heteroarylalkyl include an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteralkyl, a haloalkyl, —C(O)$NR_{28}R_{29}$, —C(S)$NR_{28}R_{29}$, —C($NR_{32}$)$NR_{28}R_{29}$, —$NR_{30}$C(O)$R_{31}$, —$NR_{30}$C(S)$R_{31}$, —$NR_{30}$C($NR_{32}$)$R_{31}$, halo, —$OR_{30}$, cyano, nitro, haloalkoxy, —C(O)$R_{30}$, —C(S)$R_{30}$, —C($NR_{32}$)$R_{30}$, —$NR_{28}R_{29}$, —C(O)$OR_{30}$, —C(S)$OR_{30}$, —C($NR_{32}$)$OR_{30}$, —OC(O)$R_{30}$, —OC(S)$R_{30}$, —OC($NR_{32}$)$R_{30}$, —$NR_{30}$C(O)$NR_{28}R_{29}$, —$NR_{30}$C(S)$NR_{28}R_{29}$, —$NR_{30}$C($NR_{32}$)$NR_{28}R_{29}$, —OC(O)$NR_{28}R_{29}$, —OC(S)$NR_{28}R_{29}$, —OC($NR_{32}$)$NR_{28}R_{29}$, —$NR_{30}$C(O)$OR_{31}$, —$NR_{30}$C(S)$OR_{31}$, —$NR_{30}$C($NR_{32}$)$OR_{31}$, —S(O)$_h R_{30}$, —OS(O)$_p R_{30}$, —$NR_{30}$S(O)$_p R_{30}$, —S(O)$_p NR_{28}R_{29}$, —OS(O)$_p NR_{28}R_{29}$, or —$NR_{30}$S(O)$_p NR_{28}R_{29}$, wherein $R_{28}$ and $R_{29}$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteralkyl; or $R_{28}$ and $R_{29}$ taken together with the nitrogen to which they are attached is optionally substituted heterocyclyl or optionally substituted heteroaryl.

$R_{30}$ and $R_{31}$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteralkyl; and $R_{32}$, for each occurrence is, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteralkyl, —C(O)$R_{30}$, —C(O)$NR_{28}R_{29}$, —S(O)$_p R_{30}$, or —S(O)$_p NR_{28}R_{29}$;

p is 1 or 2; and h is 0, 1 or 2.

In addition, alkyl, cycloalkyl, alkylene, a heterocyclyl, and any saturated portion of a alkenyl, cycloalkenyl, alkynyl, aralkyl, and heteroalkyl groups, may also be substituted with =O, =S, =N—$R_{32}$.

When a heterocyclyl, heteroaryl, or heteroaralkyl group contains a nitrogen atom, it may be substituted or unsubstituted. When a nitrogen atom in the aromatic ring of a heteroaryl group has a substituent the nitrogen may be a quaternary nitrogen.

A "straight chained hydrocarbyl group" is an alkylene group, i.e., —(CH$_2$)$_y$—, with one or more (preferably one) internal methylene groups optionally replaced with a linkage group. y is a positive integer (e.g., between 1 and 10), preferably between 1 and 6 and more preferably 1 or 2. A "linkage group" refers to a functional group which replaces a methylene in a straight chained hydrocarbyl. Examples of suitable linkage groups include a ketone (—C(O)—), alkene, alkyne, phenylene, ether (—O—), thioether (—S—), or amine (—N(R$^a$)—), wherein R$^a$ is defined below. A preferred linkage group is —C(R$_3$R$_4$)—, wherein R$_3$ and R$_4$ are defined above.

Suitable substituents for an alkylene group and a hydrocarbyl group are those which do not substantially interfere with the anti-cancer activity of the disclosed compounds. $R_3$ and $R_4$ are preferred substituents for an alkylene or hydrocarbyl group represented by Y.

An "aliphatic group" is a straight chained, branched or cyclic non-aromatic hydrocarbon which is completely saturated or which contains one or more units of unsaturation. Typically, a straight chained or branched aliphatic group has from 1 to about 20 carbon atoms, preferably from 1 to about 10, and a cyclic aliphatic group has from 3 to about 10 carbon atoms, preferably from 3 to about 8. An aliphatic group is preferably a straight chained or branched alkyl group, e.g, methyl, ethyl, n-propyl, iso-propyl, n-butyl, sec-butyl, tert-butyl, pentyl, hexyl, pentyl or octyl, or a cycloalkyl group with 3 to about 8 carbon atoms. A C1-C8 straight chained or branched alkyl group or a C3-C8 cyclic alkyl group is also referred to as a "lower alkyl" group.

The term "aromatic group" may be used interchangeably with "aromatic ring." Aromatic groups include carbocyclic aromatic groups such as phenyl, naphthyl, and anthracyl, and heteroaryl groups such as imidazolyl, thienyl, furanyl, pyridyl, pyrimidy, pyranyl, pyrazolyl, pyrroyl, pyrazinyl, thiazole, oxazolyl, and tetrazole. Aromatic groups also include fused polycyclic aromatic ring systems in which a carbocyclic aromatic ring or heteroaryl ring is fused to one or more other heteroaryl rings. Examples include benzothienyl, benzofuranyl, indolyl, quinolinyl, benzothiazole, benzooxazole, benzimidazole, quinolinyl, isoquinolinyl and isoindolyl.

As used herein, the terms "subject", "patient" and "mammal" are used interchangeably. The terms "subject" and "patient" refer to an animal (e.g., a bird such as a chicken, quail or turkey, or a mammal), preferably a mammal including a non-primate (e.g., a cow, pig, horse, sheep, rabbit, guinea pig, rat, cat, dog, and mouse) and a primate (e.g., a monkey, chimpanzee and a human), and more preferably a human. In one embodiment, the subject is a non-human animal such as a farm animal (e.g., a horse, cow, pig or sheep), or a pet (e.g., a dog, cat, guinea pig or rabbit). In a preferred embodiment, the subject is a human.

As used herein, the term "lower" refers to a group having up to four carbon atoms. For example, a "lower alkyl" refers to an alkyl radical having from 1 to 4 carbon atoms, "lower alkoxy" refers to "—O—($C_1$-$C_4$)alkyl and a "lower alkenyl" or "lower alkynyl" refers to an alkenyl or alkynyl radical having from 2 to 4 carbon atoms, respectively.

Unless indicated otherwise, the compounds of the invention containing reactive functional groups (such as (without limitation) carboxy, hydroxy, thiol, and amino moieties) also include protected derivatives thereof "Protected derivatives" are those compounds in which a reactive site or sites are blocked with one or more protecting groups. Examples of suitable protecting groups for hydroxyl groups include benzyl, methoxymethyl, allyl, trimethylsilyl, tert-butyldimethylsilyl, acetate, and the like. Examples of suitable amine protecting groups include benzyloxycarbonyl, tert-butoxycarbonyl, tert-butyl, benzyl and fluorenylmethyloxycarbonyl (Fmoc). Examples of suitable thiol protecting groups include benzyl, tert-butyl, acetyl, methoxymethyl and the like. Other suitable protecting groups are well known to those of ordinary skill in the art and include those found in T. W. Greene, Protecting Groups in Organic Synthesis, John Wiley & Sons, Inc. 1981.

As used herein, the term "compound(s) of this invention" and similar terms refers to a compound of formula (I) through (XVII) and Table 1, or a pharmaceutically acceptable salt, solvate, clathrate, hydrate, polymorph or prodrug thereof, and also include protected derivatives thereof.

The compounds of the invention may contain one or more chiral centers and/or double bonds and, therefore, exist as stereoisomers, such as double-bond isomers (i.e., geometric isomers), enantiomers, or diastereomers. According to this invention, the chemical structures depicted herein, including the compounds of this invention, encompass all of the corresponding compounds' enantiomers, diastereomers and geometric isomers, that is, both the stereochemically pure form (e.g., geometrically pure, enantiomerically pure, or diastereomerically pure) and isomeric mixtures (e.g., enantiomeric, diastereomeric and geometric isomeric mixtures). In some cases, one enantiomer, diastereomer or geometric isomer will possess superior activity or an improved toxicity or kinetic profile compared to other isomers. In those cases, such enantiomers, diastereomers and geometric isomers of compounds of this invention are preferred.

When a disclosed compound is named or depicted by structure, it is to be understood that solvates (e.g., hydrates) of the compound or its pharmaceutically acceptable salts are also included. "Solvates" refer to crystalline forms wherein solvent molecules are incorporated into the crystal lattice during crystallization. Solvate may include water or nonaqueous solvents such as ethanol, isopropanol, DMSO, acetic acid, ethanolamine, and EtOAc. Solvates, wherein water is the solvent molecule incorporated into the crystal lattice, are typically referred to as "hydrates". Hydrates include a stoichiometric or non-stoichiometric amount of water bound by non-covalent intermolecular forces.

When a disclosed compound is named or depicted by structure, it is to be understood that the compound, including solvates thereof, may exist in crystalline forms, non-crystalline forms or a mixture thereof. The compounds or solvates may also exhibit polymorphism (i.e. the capacity to occur in different crystalline forms). These different crystalline forms are typically known as "polymorphs." It is to be understood that when named or depicted by structure, the disclosed compounds and solvates (e.g., hydrates) also include all polymorphs thereof. As used herein, the term "polymorph" means solid crystalline forms of a compound of the present invention or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it. In addition, one polymorph may spontaneously convert to another polymorph under certain conditions.

When a disclosed compound is named or depicted by structure, it is to be understood that clathrates ("inclusion compounds") of the compound or its pharmaceutically acceptable salts, solvates or polymorphs are also included. As used herein, the term "clathrate" means a compound of the present invention or a salt thereof in the form of a crystal lattice that contains spaces (e.g., channels) that have a guest molecule (e.g., a solvent or water) trapped within.

As used herein and unless otherwise indicated, the term "prodrug" means a derivative of a compound that can hydrolyze, oxidize, or otherwise react under biological conditions (in vitro or in vivo) to provide a compound of this invention. Prodrugs may become active upon such reaction under biological conditions, or they may have activity in their unreacted forms. Examples of prodrugs contemplated in this invention include, but are not limited to, analogs or derivatives of compounds of formula (I) through (XVII) and Table 1 that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of formula (I) through (XVII) and Table 1, that comprise —NO, —NO$_2$, —ONO, or —ONO$_2$ moieties. Prodrugs can typically be prepared using well-known methods, such as those described by 1 BURGER'S MEDICINAL CHEMISTRY AND DRUG DISCOVERY (1995) 172-178, 949-982 (Manfred E. Wolff ed., 5$^{th}$ ed).

As used herein and unless otherwise indicated, the terms "biohydrolyzable amide", "biohydrolyzable ester", "biohydrolyzable carbamate", "biohydrolyzable carbonate", "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as improved water solubility, improved circulating half-life in the blood (e.g., because of reduced metabolism of the prodrug), improved uptake, improved duration of action, or improved onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, aminoacids, hydroxyalkylamines, heterocyclic and heteroaromatic amines, and polyether amines.

The present invention is illustrated by the following examples, which are not intended to be limiting in any way.

EXAMPLE 1

Synthesis of Compound 1

Scheme 1:

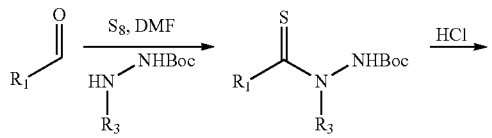

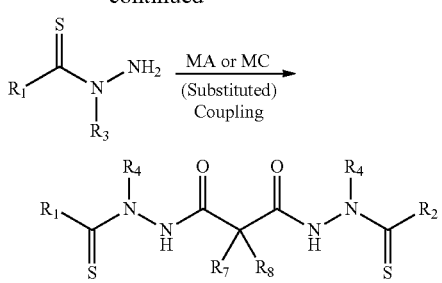

R$_1$ and R$_2$ can be the same or different.

A stirred suspension of tert-butyl-2-methylhydrazinecarboxylate (1, 5.0 mmol), benzaldehyde (5.0 mmol), sulfur powder (18 mmol) in DMF (6 mL) was heated at 140° C. for 1 h. The mixture was diluted with EtOAc (100 mL), filtered and the filtrate was washed with water (3×100 mL) and concentrated. Purification by column chromatography gave tert-butyl 2-methyl-2-(phenylcarbonothioyl)hydrazinecarboxylate (2) as an impure yellowish oil (0.45 g). Pure compound was obtained by repeated chromatography of small amount of mixture. $^1$H-NMR (CDCl$_3$) δ 8.0 (br, 1H), 7.3-7.4 (m, 5H), 3.45 (s, 3H), 1.54 (s, 9H) ppm. ESMS clcd for C$_{13}$H$_{18}$N$_2$O$_2$S: 266.1. Found: 267.1 (M+H)$^+$.

The crude product obtained above was dissolved in DCM (10 mL) and treated with TFA (0.1 mL) for 24 h at rt. The solvents was removed and the resulting mixture was purified by column chromatography to give N-methylbenzothiohydrazide (3, 87 mg) whose spectra data is identical to that previously reported.

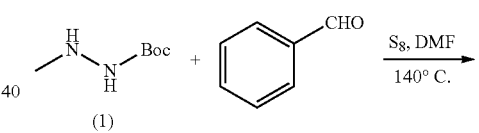

(1)

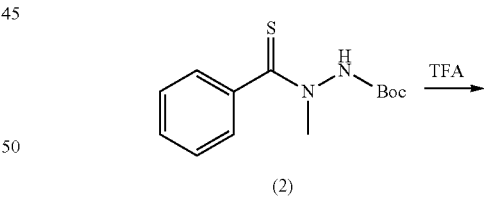

(2)

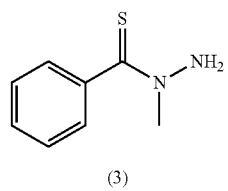

(3)

The conversion of 3 to Compound 1 has been previously reported in U.S. Pat. Nos. 6,825,235 and 7,074,952, the entire teachings of which are incorporated by reference herein.

Data of Other Analogs and Intermediates:

N-methylpyridine-3-carbothiohydrazide

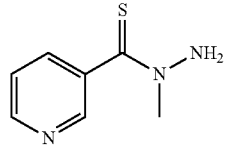

$^1$H-NMR (CDCl$_3$) δ 8.60 (s, 2H), 7.7 (d, 1H, J=8), 7.3 (t, 1H, J=4), 5.97 (s, 2H), 3.40 (s, 3H) ppm. ESMS clcd for C$_7$H$_9$N$_3$S: 167.1. Found: 168.1 (M+H)$^+$.

N'1,N'3-dimethyl-N'1,N'3-di(pyridine-3-carbonothioyl)malonohydrazide

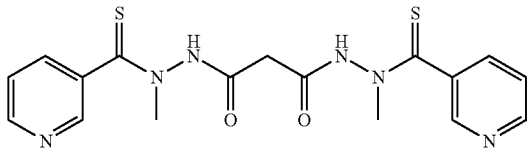 [SMILES: CN(NC(=O)CC(=O)NN(C)C(=S)c1cccnc1)C(=S)c1cccnc1]

$^1$H-NMR (CDCl$_3$) δ 8.7 (m, 2H), 8.5 (m, 2H), 7.8 (m, 2H), 7.4 (m, 2H), 3.0-3.8 (m, 8H) ppm. ESMS clcd for C$_{17}$H$_{18}$N$_6$O$_2$S$_2$: 402.1. Found: 403.1 (M+H)$^+$.

N-methylpyridine-4-carbothiohydrazide

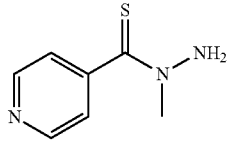

$^1$H-NMR (CDCl$_3$) δ 8.60 (d, 2H, J=5), 7.7 (d, 2H, J=5), 5.93 (s, 2H), 3.34 (s, 3H) ppm. ESMS clcd for C$_7$H$_9$N$_3$S: 167.1. Found: 168.1 (M+H)$^+$.

N'1,N'3-dimethyl-N'1,N'3-di(pyridine-4-carbonothioyl)malonohydrazide

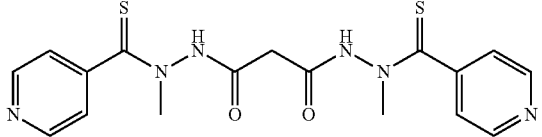 [SMILES: CN(NC(=O)CC(=O)NN(C)C(=S)c1ccncc1)C(=S)c1ccncc1]

$^1$H-NMR (CD$_3$OD) δ 8.5 (d, 4H, J=5), 7.2 (d, 4H, J=5), 4.7 (br, 2H), 3.63 (s, 6H), 3.36 (s, 2H) ppm. ESMS clcd for C$_{17}$H$_{18}$N$_6$O$_2$S$_2$: 402.1. Found: 403.1 (M+H)$^+$.

While this invention has been particularly shown and described with references to preferred embodiments thereof, it will be understood by those skilled in the art that various changes in form and details may be made therein without departing from the scope of the invention encompassed by the appended claims.

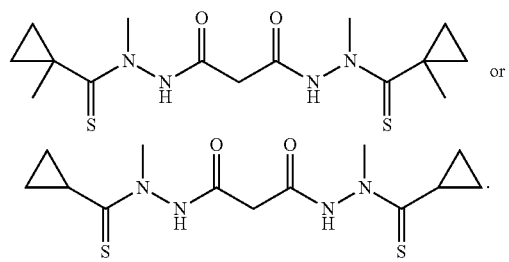

What is claimed is:

1. A method of preparing a bis(thio-hydrazide amide) represented by formula (I):

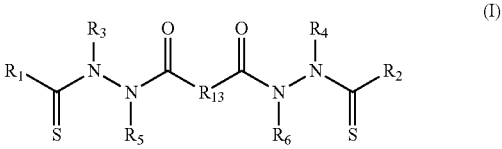

or a tautomer, pharmaceutically acceptable salt, or prodrug thereof, wherein:
R$_{13}$ is a covalent bond, or a substituted or unsubstituted C1-C6 alkylene group;
R$_1$ and R$_2$ are independently an optionally substituted aryl or an optionally substituted heteroaryl;
R$_3$ and R$_4$ are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl or an optionally substituted heteroaryl;
R$_5$ and R$_6$ are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl or an optionally substituted heteroaryl;
R$_{40}$ is an optionally substituted aryl or an optionally substituted heteroaryl; and
R$_{41}$ is —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl or an optionally substituted heteroaryl; comprising
a) reacting a compound of formula (V):

with S$_8$, DMF and a compound of formula (VI):

b) deprotecting the resulting compound; and
c) coupling the deprotected compound obtained in step b) to obtain a compound of formula (I).

2. The method of claim 1, wherein
R$_5$ is —H and R$_6$ is —H, an optionally substituted alkyl, an optionally substituted alkenyl, an optionally substituted alkynyl, an optionally substituted cycloalkyl, an optionally substituted cycloalkenyl, an optionally substituted heterocyclyl; and
R$_3$ and R$_4$ are each an alkyl group.

3. The method of claim 2, wherein R$_1$ and R$_2$ are each a substituted or unsubstituted phenyl group and R$_3$ and R$_4$ are each methyl or ethyl; or $R_1$ and $R_2$ are each an optionally substituted pyridyl group and $R_3$ and $R_4$ are each methyl or ethyl.

4. The method of claim 1, wherein
$R_{13}$ is —C($R_7$)($R_8$)—;
$R_7$ and $R_8$ are each independently —H or an optionally substituted alkyl, an optionally substituted alkenyl, an optionally substituted alkynyl, an optionally substituted cycloalkyl, an optionally substituted cycloalkenyl, an optionally substituted heterocyclyl, or $R_7$ is —H and $R_8$ is an optionally substituted aryl or an optionally substituted heteroaryl.

5. The method of claim 1, wherein the compound is represented by formula (III):

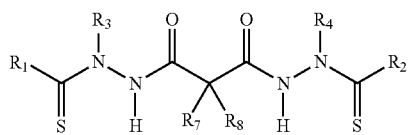

(III)

wherein:
$R_7$ and $R_8$ are each independently —H or an optionally substituted alkyl, an optionally substituted alkenyl, an optionally substituted alkynyl, an optionally substituted cycloalkyl, an optionally substituted cycloalkenyl, an optionally substituted heterocyclyl, or $R_7$ is —H and $R_8$ is an optionally substituted aryl or an optionally substituted heteroaryl.

6. The method of claim 5, wherein:
$R_1$ and $R_2$ are both phenyl; $R_3$ and $R_4$ are both methyl; $R_7$ and $R_8$ are both —H;
$R_1$ and $R_2$ are both phenyl; $R_3$ and $R_4$ are both ethyl; $R_7$ and $R_8$ are both —H;
$R_1$ and $R_2$ are both 4-cyanophenyl; $R_3$ and $R_4$ are both methyl; $R_7$ is methyl; $R_8$ is —H;
$R_1$ and $R_2$ are both 4-methoxyphenyl; $R_3$ and $R_4$ are both methyl; $R_7$ and $R_8$ are both —H;
$R_1$ and $R_2$ are both phenyl; $R_3$ and $R_4$ are both methyl; $R_7$ is methyl; $R_8$ is —H;
$R_1$ and $R_2$ are both phenyl; $R_3$ and $R_4$ are both ethyl; $R_7$ is methyl; $R_8$ is —H;
$R_1$ and $R_2$ are both 4-cyanophenyl; $R_3$ and $R_4$ are both methyl; $R_7$ and $R_8$ are both —H;
$R_1$ and $R_2$ are both 2,5-dimethoxyphenyl; $R_3$ and $R_4$ are both methyl; $R_7$ and $R_8$ are both —H;
$R_1$ and $R_2$ are both 2,5-dimethoxyphenyl; $R_3$ and $R_4$ are both methyl; $R_7$ is methyl;
$R_8$ is —H;
$R_1$ and $R_2$ are both 3-cyanophenyl; $R_3$ and $R_4$ are both methyl; $R_7$ and $R_8$ are both —H;
$R_1$ and $R_2$ are both 3-fluorophenyl; $R_3$ and $R_4$ are both methyl; $R_7$ and $R_8$ are both —H;
$R_1$ and $R_2$ are both 4-chlorophenyl; $R_3$ and $R_4$ are both methyl; $R_7$ is methyl; $R_8$ is —H;
$R_1$ and $R_2$ are both 2-dimethoxyphenyl; $R_3$ and $R_4$ are both methyl; $R_7$ and $R_8$ are both —H;
$R_1$ and $R_2$ are both 3-methoxyphenyl; $R_3$ and $R_4$ are both methyl; $R_7$ and $R_8$ are both —H;
$R_1$ and $R_2$ are both 2,3-dimethoxyphenyl; $R_3$ and $R_4$ are both methyl; $R_7$ and $R_8$ are both —H;
$R_1$ and $R_2$ are both 2,3-dimethoxyphenyl; $R_3$ and $R_4$ are both methyl; $R_7$ is methyl;
$R_8$ is —H;
$R_1$ and $R_2$ are both 2,5-difluorophenyl; $R_3$ and $R_4$ are both methyl; $R_7$ and $R_8$ are both —H;

$R_1$ and $R_2$ are both 2,5-difluorophenyl; $R_3$ and $R_4$ are both methyl; $R_7$ is methyl;
$R_8$ is —H;
$R_1$ and $R_2$ are both 2,5-dichlorophenyl; $R_3$ and $R_4$ are both methyl; $R_7$ and $R_8$ are both —H;
$R_1$ and $R_2$ are both 2,5-dimethylphenyl; $R_3$ and $R_4$ are both methyl; $R_7$ and $R_8$ are both —H;
$R_1$ and $R_2$ are both 2,5-dimethoxyphenyl; $R_3$ and $R_4$ are both methyl; $R_7$ and $R_8$ are both —H;
$R_1$ and $R_2$ are both phenyl; $R_3$ and $R_4$ are both methyl; $R_7$ and $R_8$ are both —H; or $R_1$ and $R_2$ are both 2,5-dimethoxyphenyl; $R_3$ and $R_4$ are both methyl; $R_7$ is methyl;
$R_8$ is —H.

7. The method of claim 1, wherein the compound of formula (I) is

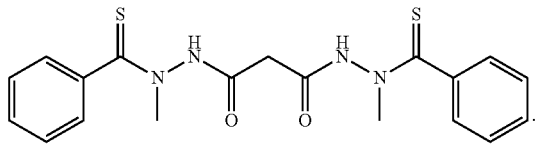 [SMILES: CN(NC(=O)CC(=O)NN(C)C(=S)c1ccccc1)C(=S)c1ccccc1]

8. A method of preparing a bis(thio-hydrazide amide) represented by formula (II):

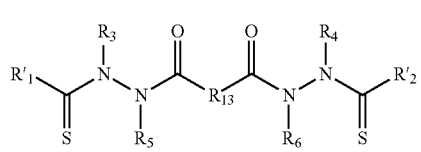

(II)

or a tautomer, pharmaceutically acceptable salt, or prodrug thereof, wherein:
$R_{13}$ is a covalent bond, or a substituted or unsubstituted C1-C6 alkylene group;
$R'_1$ and $R'_2$ are independently an optionally substituted alkyl, an optionally substituted alkenyl, an optionally substituted alkynyl, an optionally substituted cycloalkyl, an optionally substituted cycloalkenyl, or an optionally substituted heterocyclyl;
$R_3$ and $R_4$ are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl or an optionally substituted heteroaryl;
$R_5$ and $R_6$ are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl or an optionally substituted heteroaryl;
$R'_{40}$ is an optionally substituted alkyl, an optionally substituted alkenyl, an optionally substituted alkynyl, an optionally substituted cycloalkyl, an optionally substituted cycloalkenyl, or an optionally substituted heterocyclyl; and
$R_{41}$ is —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl or an optionally substituted heteroaryl; comprising a) reacting a compound of formula (VII):

with $S_8$, DMF and a compound of formula (VI):

b) deprotecting the resulting compound; and
c) coupling the deprotected compound obtained in step b) to obtain a compound of formula (II).

9. The method of claim 8, wherein $R_3$ and $R_4$ are each an optionally substituted alkyl, an optionally substituted alkenyl, an optionally substituted alkynyl, an optionally substituted cycloalkyl, an optionally substituted cycloalkenyl, or an optionally substituted heterocyclyl; and
$R_5$ is —H; and
$R_6$ is —H or an optionally substituted alkyl, an optionally substituted alkenyl, an optionally substituted alkynyl, an optionally substituted cycloalkyl, an optionally substituted cycloalkenyl, an optionally substituted heterocyclyl.

10. The compound of claim 9, wherein $R'_1$ and $R'_2$ are both a C3-C8 cycloalkyl group optionally substituted with at least one alkyl group; $R_3$ and $R_4$ are both an alkyl group; and $R_6$ is —H or methyl.

11. The compound of claim 10, wherein $R'_1$ and $R'_2$ are both cyclopropyl or 1-methylcyclopropyl.

12. The method of claim 8, wherein $R_{13}$ is —C($R_7$)($R_8$)—; $R_7$ and $R_8$ are each independently —H or an optionally substituted alkyl, an optionally substituted alkenyl, an optionally substituted alkynyl, an optionally substituted cycloalkyl, an optionally substituted cycloalkenyl, an optionally substituted heterocyclyl, or $R_7$ is —H and $R_8$ is an optionally substituted aryl or an optionally substituted heteroaryl.

13. The method of claim 8, wherein the compound is represented by formula (IV):

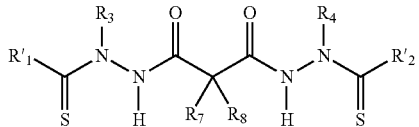

wherein:
$R_7$ and $R_8$ are each independently —H or an optionally substituted alkyl, an optionally substituted alkenyl, an optionally substituted alkynyl, an optionally substituted cycloalkyl, an optionally substituted cycloalkenyl, an optionally substituted heterocyclyl, or $R_7$ is —H and $R_8$ is an optionally substituted aryl or an optionally substituted heteroaryl.

14. The method of claim 13, wherein:
$R'_1$ and $R'_2$ are both cyclopropyl; $R_3$ and $R_4$ are both methyl; $R_7$ and $R_8$ are both —H;
$R'_1$ and $R_2$ are both cyclopropyl; $R_3$ and $R_4$ are both ethyl; $R_7$ and $R_8$ are both —H;
$R'_1$ and $R'_2$ are both cyclopropyl; $R_3$ and $R_4$ are both methyl; $R_7$ is methyl; $R_8$ is —H;
$R_1$ and $R'_2$ are both 1-methylcyclopropyl; $R_3$ and $R_4$ are both methyl; $R_7$ and $R_8$ are both —H;
$R'_1$ and $R'_2$ are both 1-methylcyclopropyl; $R_3$ and $R_4$ are both methyl; $R_7$ is methyl and $R_8$ is —H;
$R'_1$ and $R'_2$ are both 1-methylcyclopropyl; $R_3$ and $R_4$ are both methyl; $R_7$ is ethyl and $R_8$ is —H;
$R'_1$ and $R'_2$ are both 1-methylcyclopropyl; $R_3$ and $R_4$ are both methyl; $R_7$ is n-propyl and $R_8$ is —H;
$R'_1$ and $R'_2$ are both 1-methylcyclopropyl; $R_3$ and $R_4$ are both methyl; $R_7$ and $R_8$ are both methyl;
$R'_1$ and $R'_2$ are both 1-methylcyclopropyl; $R_3$ and $R_4$ are both ethyl; $R_7$ and $R_8$ are both —H;
$R'_1$ and $R'_2$ are both 1-methylcyclopropyl; $R_3$ is methyl, and $R_4$ is ethyl; $R_7$ and $R_8$ are both —H;
$R'_1$ and $R'_2$ are both 2-methylcyclopropyl; $R_3$ and $R_4$ are both methyl; $R_7$ and $R_8$ are both —H;
$R'_1$ and $R'_2$ are both 2-phenylcyclopropyl; $R_3$ and $R_4$ are both methyl; $R_7$ and $R_8$ are both —H;
$R'_1$ and $R'_2$ are both 1-phenylcyclopropyl; $R_3$ and $R_4$ are both methyl; $R_7$ and $R_8$ are both —H;
$R'_1$ and $R'_2$ are both cyclobutyl; $R_3$ and $R_4$ are both methyl; $R_7$ and $R_8$ are both —H;
$R_1$ and $R_2$ are both cyclopentyl; $R_3$ and $R_4$ are both methyl; $R_7$ and $R_8$ are both —H;
$R'_1$ and $R'_2$ are both cyclohexyl; $R_3$ and $R_4$ are both methyl; $R_7$ and $R_8$ are both —H;
$R'_1$ and $R'_2$ are both cyclohexyl; $R_3$ and $R_4$ are both phenyl; $R_7$ and $R_8$ are both —H;
$R'_1$ and $R'_2$ are both methyl; $R_3$ and $R_4$ are both methyl; $R_7$ and $R_8$ are both —H;
$R'_1$ and $R'_2$ are both methyl; $R_3$ and $R_4$ are both t-butyl; $R_7$ and $R_8$ are both —H;
$R'_1$ and $R'_2$ are both methyl; $R_3$ and $R_4$ are both phenyl; $R_7$ and $R_8$ are both —H;
$R'_1$ and $R'_2$ are both t-butyl; $R_3$ and $R_4$ are both methyl; $R_7$ and $R_8$ are both —H;
$R'_1$ and $R'_2$ are ethyl; $R_3$ and $R_4$ are both methyl; $R_7$ and $R_8$ are both —H; or
$R'_1$ and $R'_2$ are both n-propyl; $R_3$ and $R_4$ are both methyl; $R_7$ and $R_8$ are both —H.

15. The method of claim 8, wherein the compound of formula (II) is